United States Patent [19]

Jones

[11] Patent Number: 4,607,766

[45] Date of Patent: Aug. 26, 1986

[54] ESCAPEMENT DEVICE

[75] Inventor: J. Paul Jones, Glenmoore, Pa.

[73] Assignee: Med-Tech Associates, Broomall, Pa.

[21] Appl. No.: 723,563

[22] Filed: Apr. 15, 1985

[51] Int. Cl.$^4$ .............................................. B67D 3/00
[52] U.S. Cl. .................................. 222/386.5; 222/453; 222/504; 604/249; 604/414
[58] Field of Search ................. 222/386, 386.5, 424.5, 222/425, 449–451, 453, 476, 504, 372; 604/33, 246, 249, 254, 411, 414

[56] References Cited

U.S. PATENT DOCUMENTS

| | | | |
|---|---|---|---|
| 2,254,833 | 9/1941 | Ashkenaz | 604/249 X |
| 3,072,302 | 1/1963 | Giovannoni et al. | 222/453 X |
| 3,199,747 | 8/1965 | Erickson | 222/504 X |
| 4,015,755 | 4/1977 | Lerner et al. | 222/442 |

FOREIGN PATENT DOCUMENTS

| | | | |
|---|---|---|---|
| 499115 | 1/1939 | United Kingdom | 222/453 |
| 1005693 | 9/1965 | United Kingdom | 222/504 |

Primary Examiner—Joseph J. Rolla
Assistant Examiner—Michael S. Huppert
Attorney, Agent, or Firm—Frederick J. Olsson

[57] ABSTRACT

For an intervenous infusion system and the like, an escapement device to be disposed between a source of fluid and a receiver of fluid. The device allows fluid to escape from the source and then intermittently takes a fixed, measured quantity of such fluid and transfers that quantity to the receiver.

5 Claims, 7 Drawing Figures

ESCAPEMENT DEVICE

This invention relates in general to fluid control devices and in particular relates to a device to be disposed between a source of fluid and a receiver of fluid which functions to extract fluid from the source and intermittently transfer identical amounts of fluid to the receiver.

The device allows fluid to escape from the source and then intermittently takes a fixed, measured quantity of such fluid and transfers that quantity to the receiver. The structure of the escapement device will be described in connection with an intervenous infusion system. It will be understood, however, that the device finds utility in other environments such as in laboratories where small but accurate measures of fluid are used in automatic blood testing machines and the like.

The device is described below in connection with the accompanying drawings wherein:

In FIG. 1, the components are in a first or start position.

Figure 1:
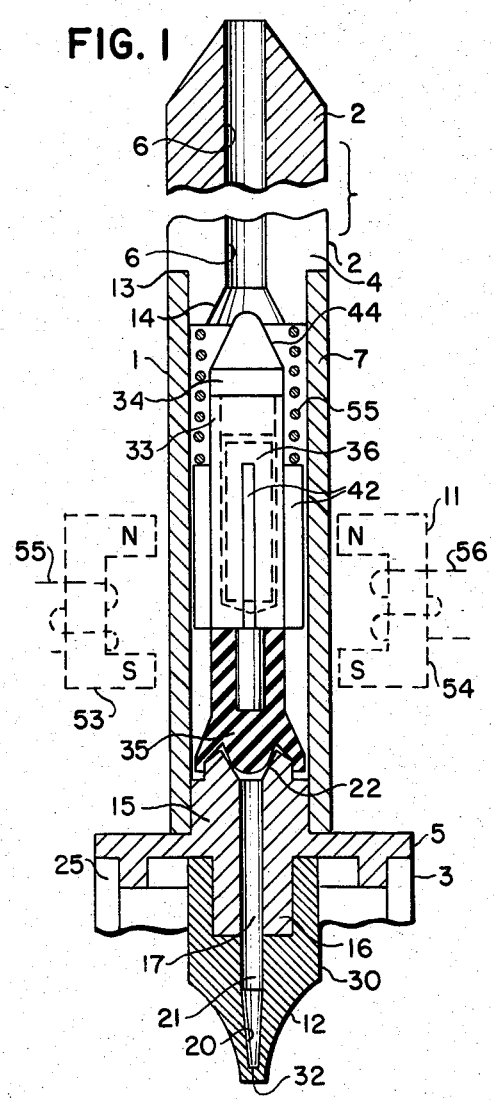
FIG. 1 is an elevational view partially in section and shows the escapement device mounted between the spike and drip chamber of an intervenous system wherein the spike and cap of the drip chamber have been modified to incorporate certain components of the escapement device.

In FIG. 1 the escapement device 1 is shown disposed between a spike 2 and a drip chamber 3 of an intervenous infusion system.

The spike 2 is of conventional form except modifications have been incorporated in the bottom end 4 as will be explained later. The drip chamber 3 is also of conventional form except modifications have been incorporated in the cap 5 as will be explained later. Also, the drip chamber, with such modifications, may be of the type shown in my copending application Ser. No. 674,036 filed 11/23/84 and entitled "Plug Valve" and in copending application Ser. No. 674,406 filed 11/23/84 and entitled "Means for Counting Drops".

In an intervenous system the source of fluid conventionally is a plastic bag and the tapered end of a spike is inserted into the bag and receives fluid therefrom. In the present arrangement the spike 2 has such a tapered end, and fluid from the spike flows to the drip chamber via bore 6. Also, in an intervenous infusion system, the receiver or receiving system includes a drip chamber and a plastic line for carrying fluid from the drip chamber to a needle at the end of the line, which is inserted in the patient's body.

In a conventional infusion system the total amount of fluid injected into a patient's body is determined by the number of drips entering the receiving system over a given period of time. Obviously, if the quantity or volume of fluid differs, as between drops, and the number of drops is not accurately counted, the total amount injected will be in error. Nonuniform volume of drops, and inaccurate drop rates are common problems with noncontrolled infusion systems.

The prime purpose of the escapement device of the invention is to insure that the quantity or volume of each drop transferred to the receiving system is accurate and identical.

As noted above, uncontrolled systems for setting the rates of drops are inaccurate. Means for accurately counting drops is shown in my copending application Ser. No. 674,406.

With the above facts in mind, I will now describe the structure of the escapement device.

The escapement device 1 includes: an escapement cylinder 7 connected between the spike bottom 4 and drip chamber cap 5; a shuttle 10 mounted inside of the escapement cylinder for reciprocating up and down along the axis of the cylinder by magnetic drive means 11 and a one-way check valve 12.

Figure 2:
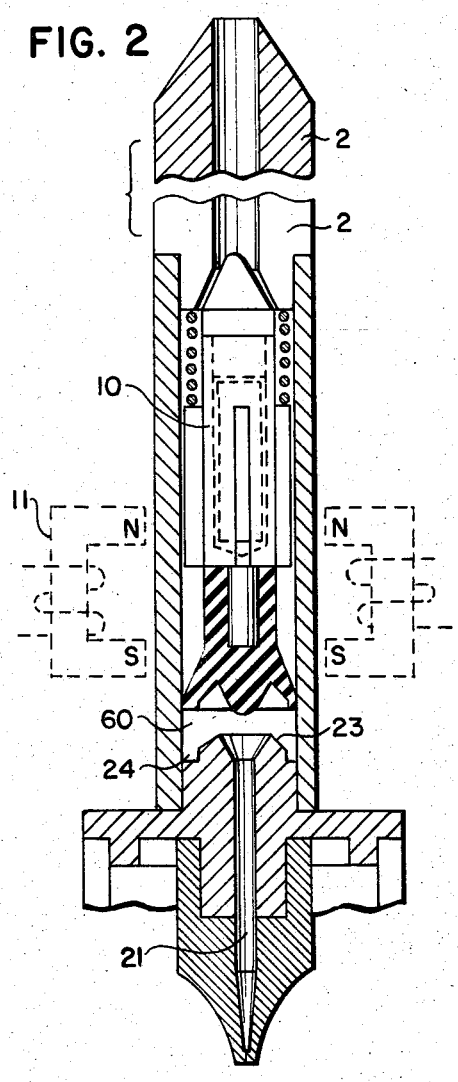
FIG. 2 is a view like FIG. 1 except that the components are in a second or momentary stop position.

The shuttle is repeatedly driven from a first or start position as shown in FIG. 1 upwardly to a second or momentary stop position as shown in FIG. 2 and then back down to the first position by a magnetic field generated by the magnetic cores 11 and drive coils 55 and 56, which interact with the permanent magnet 36 in the shuttle body 33.

The reciprocating motion of the shuttle assembly 10 provides for the escapement cylinder 7 to receive a volume of fluid from the source (via bore 6) to the volumetric chamber 60, and thence to the receiver or drip chamber 3 (via valve 12). The amount of fluid transferred on each reciprocal stroke is always the same. By counting the number of accurate drops from valve 12, the actual volume of fluid transferred to the receiving system (patient) is easily determined.

The novel modifications to the spike 2 and to the cap 5 of the drip chamber 3 will now be explained.

Referring to FIG. 1, the bottom 4 of the spike has an annular shoulder 13 which receives the escapement cylinder 7. At the lower end of the bore 6 there is a conically shaped surface which forms a fluid intake valve seat means 14. The seat means 14 is co-axial with the axis of the escapement cylinder. The manner in which the seat means 14 functions will be explained later.

Figure 6:
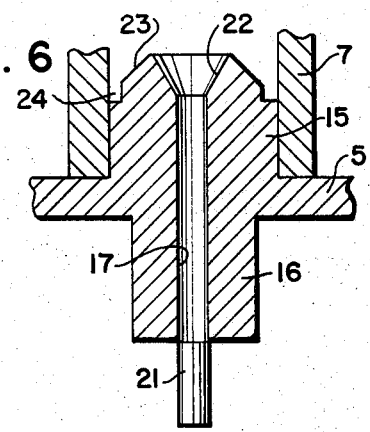
FIG. 6 is an enlarged, fragmentary elevational view partially in section illustrating the modified drip chamber cap.
Figure 7:
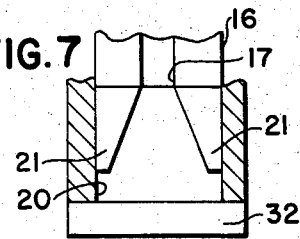
FIG. 7 is a fragmentary, elevational view partially in section further illustrating the modified drip chamber cap from a side view.

Referring to FIG. 6 the cap 5 has an upper cylindrical extension 15 extending up into the escapement cylinder 7 and a lower cylindrical extension 16 extending down into the drip chamber 3. The upper and lower extensions 15 and 16 have the drip passageway 17. As noted in FIGS. 1 and 2 the lower extension 16 carries the check valve 12 which has an exit passage 20 in communication with the fluid passageway 17. The passages 17 and 20 carry fluid from the escapement cylinder 7 and chamber 60 into the drip chamber 3. The lower extension 16 has a pair of ears 21, the purpose of which will be noted later.

The upper extension 15 is formed with conically shaped surface which forms fluid discharge valve seat means 22 which is coaxial with the axis of the escapement cylinder 7 and in communication with the drip passageway 17. The functioning of the seat means 22 will be explained later.

The upper extension 15 is also formed with a second conically shaped surface 23 which is coaxial with the axis of the escapement cylinder. An annular shoulder on the extension cooperates with the inside of the escapement cylinder to form an annular cavity 24. The function of the conical surface 23 and cavity 24 will be explained later.

Except as noted following, the check valve 12 is of conventional form comprising a cylindrical portion 30 which receives the lower extension 16 and tapered ears 21.

The exit passage 20 is formed both in the cylindrical portion 30 and in the tapered portion 31. In cross-section, the exit passage 20 is generally rectangular in shape and is configured to receive the ears 21 which form portions of the exit passage. The lower end of tapered portion 20 has a slit 32 from which the fluid exits.

The structure of the shuttle means 10 will now be described.

Figure 4:
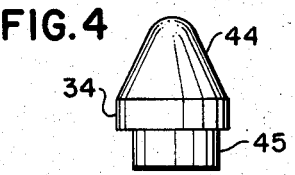
FIG. 4 is an elevational view of a nose piece comprising a part of the shuttle means used in the device of FIG. 1.
Figure 3:
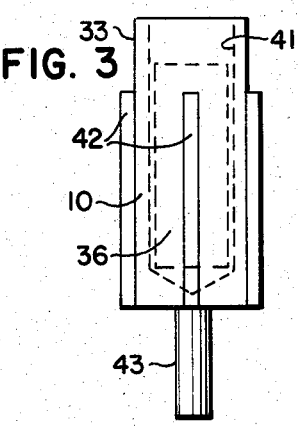
FIG. 3 is an elevational view of a body piece comprising a part of the shuttle means used in the device of FIG. 1.
Figure 5:
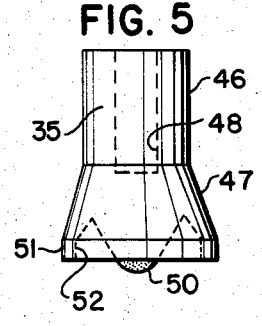
FIG. 5 is an elevational view of a fluid control mechanism comprising a part of the shuttle means used in the device of FIG. 1.

The shuttle means 10 comprises four parts, namely: a body piece 33; a plug piece 34; a fluid control piece 35; and a permanent magnet 36 inside of the shuttle. The body piece 33, the plug piece 34, and fluid control piece 35 are shown in exploded array in FIGS. 3, 4, & 5.

The body piece 33 has a bore 41 which is fitted with the magnet 36. There are guides 42 which slidingly engage the inside wall of the escapement cylinder 7 and guide the shuttle for reciprocating motion along the axis of the escapement cylinder. The lower end of the body piece 33 carries a mounting extension 43.

The plug piece 34 has a conically shaped surface 44 and a mounting extension 45 which (see FIGS. 1 and 2) fits down into the bore 41, the surface 44 forming a valve with the valve seat 14.

The fluid control piece 35 has a cylindrically shaped upper section 46 and a lower tapered section 47. The upper section 46 has a bore 48 by which the fluid control piece is press fitted on the extension 43.

The lower tapered section 47 has a conically shaped flexible outer surface and an inside surface which forms fluid discharge plug means 50 and a conically shaped skirt 51 which surrounds the discharge plug means 50. The outer perimeter of the skirt 51 has an annular lip 52 which (see FIGS. 1 and 2) is closely adjacent the inside wall of the escapement cylinder to provide a small annular space between the wall and the lip.

The drive mechanism means 11 will now be explained.

The drive mechanism includes a pair of U-shaped cores 53 and 54, pole forming windings 55 and 56 respectively on the cores 53 and 54, and permanent magnet 36 within the shuttle means 10. In certain instances the drive may include a compression spring such as spring 55 extending between guides 42 and the spike bottom 4.

The details of component arrangement and of operation of a drive mechanism of the kind in question is shown in my copending application Ser. No. 674,185 filed Nov. 23, 1984 and entitled "Linear Impulse Motor". Thus, the description herein will concern the components of the drive particularly with respect to moving the shuttle means 10.

Referring to the cores 52 and 53 and the respective drive windings 54 and 55, it is pointed out that each winding is arranged so that when energized the north and south poles are formed as noted by the letters N and S. In connection with that arrangement the permanent magnet 36 is set up in the body piece so that its north pole is at the top and the south pole is at the bottom.

As noted in FIGS. 1 and 2, the cores 52 and 53 are disposed respectively on opposite sides of the escapement cylinder 7 with the respective north and south poles facing one another. The cores lie in and are symmetrical with a vertical plane which contains the axis of the escapement cylinder.

In the first position as shown in FIG. 1 the shuttle means 10 positions the lower or south pole of the magnet 36 midway between the north and south poles of the cores 52 and 53. In the up or second position the components of the shuttle position the lower or south poles of the magnet 36 is in approximate alignment with the north poles of the cores 52 and 53.

The windings 53 and 54 are energized by short duration pulses. A pulse is applied when the shuttle is in the first position of FIG. 1 and the reaction with the permanent magnet 36 causes the shuttle to quickly move to the second position of FIG. 2. The drive pulse turns off when the shuttle is in the second position. Thereafter the position of the south pole of the magnet 36 with respect to the cores 53 and 54 causes the magnet 36 to drive the shuttle down to the first position. As previously noted, the down force may be augmented by the use of the spring 55. The spring 54 is compressed when the shuttle is moved up to the second position of FIG. 2, and has a small bias pressure in the first resting position to maintain a good seal.

The cores 53 and 54 are mounted in a housing not shown. The housing is C-shaped and the center aperture is dimensioned to a sliding sideways fit with escapement cylinder 7. The open part of the C-shape permits the spike tip and escapement cylinder to be snapped into position without touching the housing; which could cause a possible loss of sterility of the spike. It is also both convenient and necessary to plug the spike 2 into the fluid source first, which would preclude a conventional solenoid coil with a circular aperture which would have to be pierced by the spike.

The operation of the escapement device to transfer fixed amounts of fluid from the source to the receiver will now be described.

Assume that the components are in the first position. It will be noted that the fluid intake plug means 44 is spaced down away from the fluid intake valve seat means 14 and that the fluid discharge plug means 50 engages the fluid discharge valve seat means 22. Fluid from the source has filled the spike bore 6, the area created by the conical surface 14, the inside of the escapement cylinder 7, the drip passage way 17, and the exit passage 20.

Current pulses are applied to the windings 53 and 54 and the shuttle is moved to the second position. On the way, fluid is drawn into the volumetric chamber 60 past the control piece lip 52. The engaging of the fluid intake plug 44 with intake valve seat 14 prevents momentary feed through of fluid for the duration of the drive pulse, making the movement relatively immune to drive pulse duraction, beyond a required mininum.

Also, in the second position the fluid discharge plug means 50 is spaced away from the fluid discharge valve seat means. In this position the fluid discharge valve seat means 22, the fluid discharge plug means 50, the skirt 51, the lip 52, and the inside wall of the escapement cylinder 7 form a volumetric fluid measuring chamber 60.

As the shuttle means is moved from the first position to the second position, the conical shape of the skirt 51, the flexibility of the skirt 51, and the space between the lip 52 and the inside wall of the escapement cylinder 7 permit fluid in the escapement cylinder to pass through the space and flow into the volumetric measuring chamber 60.

Referring to the check valve 12, the instant the shuttle means 10 starts to move upwardly the slit 32 tightly closes trapping the fluid in the exit passage 20 and the drip passageway 17.

Thus, it will be seen that each time the shuttle moves from the first position up to the second position, the same amount of fluid enters the volumetric chamber 60. The amount of fluid in chamber 60 is subsequently discharged out through the slit 32.

The drops coming out of the slit 32 each have the same volume.

The manner in which the fluid is discharged will next be described.

When the shuttle means 10 moves down from the second position the conical shape of the skirt 51, the flexibility of the skirt 51, and the fluid in the chamber 60 cause the skirt to expand outwardly placing the lip 52 against the inside wall of the escapement cylinder. The contact between the lip and the inside wall can be characterized as forming a sliding seal. As the shuttle moves down the fluid in chamber 60 is discharged into the drip passageway 17 and the exit passage 20 and out through the slit 32.

Further, in connection with the downward movement, the disengagement of the fluid intake plug 44 from the fluid intake valve seat means 14 permits fluid from the source to flow into the escapement cylinder.

In connection with the discharge of fluid from the chamber 60, the design purges any air bubbles which may be initially trapped in the chamber. This purging is effected by the lip 52 entering the cavity 24 and by that the conical surface 23 is in close proximity with the inside conical surface of the skirt 51. In addition, the purging design acts to prime the entire system with fluid when the fluid source is first connected.

Further, in connection with minimizing buttle formation, the ears 21 forming a tapered transition between drip passage 16 and exit transition were abrupt and formed a pocket without the ears 21.

Before closing, I will comment on the preferred materials used for the various components and also on relative dimensions.

The excapement cylinder 7, the spike 2, and the cap 5 are molded from medical grade acryllic resin and are sonically welded together. In one embodiment of the device the escapement cylinder is 1.285 inches in length with an inside diameter of 0.275 inches and wall thickness of 0.050 inches.

The body piece 33, and plug piece 34 are made from medical grade acryllic resin. The body piece 33 and plug piece 34 are also sonically welded together, and seal in the press fit permanent magnet of alnico.

The fluid control piece 35 and check valve 12 is made of medical grade silicon rubber.

The conical surface on the plug piece 34 forms the fluid intake plug means 34 and the conical surface of the spike 2 forms the fluid intake valve seat are angled at about 65°. Approximately the same angle is used for the fluid discharge plug means 56 and the fluid discharge valve seat 22.

The conical surface 23 and the corresponding inside conical surface on the lip 51 are at approximately a 40° angle.

I claim:
1. In an intervenous infusion system:
a drip chamber including a cap on the top thereof;
a connection spike;
escapement means connected between the drip chamber and spike for extracting fluid from the spike and intermittently transferring identical amounts of said fluid to said drip chamber, the escapement means comprising:
an elongated, hollow escapement cylinder, the bottom end of which is connected to the cap of said drip chamber and the top end of which is connected to said spike to extend vertically upwardly when said drip chamber is mounted for use;
elongated shuttle means inside of said escapement cylinder;
guide means on said shuttle engaging the inside wall of said escapement cylinder mounting the shuttle for reciprocating motion along the axis of the escapement cylinder;
conically shaped fluid intake plug means connected to and disposed at the top end of said shuttle;
fluid control mechanism made of flexible material and connected to and disposed at the bottom end of said shuttle and formed with conically shaped fluid discharge plug means;
first means on said cap formed with a conically shaped fluid discharge valve seat means coaxial with the axis of said escapement cylinder to be engaged and disengaged by said discharge plug means and also formed with a drip passageway to pass fluid to said drip chamber;
second means on said spike formed with conically shaped fluid intake valve seat means coaxial with the axis of said escapement cylinder to be engaged and disengaged by said intake plug means;
said shuttle means being dimensioned to permit passage of fluid through said escapement cylinder as between said fluid intake valve seat means and said fluid discharge valve seat means;
said fluid control mechanism also formed with conically shaped skirt surrounding said discharge plug means, the outer perimeter of the skirt having an annular lip closely adjacent to the inside wall of said escapement cylinder to provide an annular space between the wall and the lip;
drive means for moving said shuttle from a first position to a second position, the first position being below said second position:
(a) in the first position said fluid intake plug means being spaced away from said fluid intake valve seat means and said fluid discharge valve plug means engaging said fluid discharge valve seat means;
(b) in the second position said fluid intake plug means engaging said fluid intake valve seat means and said fluid discharge plug means being spaced away from said fluid discharge valve seat means, the fluid discharge valve seat means, the fluid discharge plug means, the skirt and lip, and the inside wall of the escapement cylinder forming a volumetric fluid measuring chamber;
when said shuttle is moving from said first position up to said second position:

(a) said conical shape of said skirt, said flexibility of said skirt, and said space between said lip and the inside wall of said escapement cylinder functioning to permit fluid to pass through the space and flow into said volumetric measuring chamber until said fluid intake plug means engages said fluid intake valve seat means;

when said shuttle is moving from said second position down to said first position:

(a) said conical shape of said skirt and said flexibility of said skirt and fluid in said volumetric measuring chamber causing the said lip to slidingly seal against the inside wall of said escapement cylinder so that fluid in said volumetric measuring chamber is pushed out of the volumetric measuring chamber until said discharge plug means engages said discharge seat means; and (b) the movement of said fluid intake plug means away from said fluid intake valve means permitting new fluid to flow into said escapement cylinder; and check valve means connected to said cap and having an exit passage in series with said drip passage way, the check valve means functioning when the shuttle is moving from said second position down to said first position to permit fluid in the drip passageway to flow through the exit passage into said drip chamber and functioning when said shuttle is moving from said first position up to said second position to stop any backflow of fluid in the exit passage.

2. The construction of claim 1 wherein said first means on said cap is further formed with:

a conical surface coaxial with the axis of said escapement cylinder and facing said skirt and with one portion of an annular cavity, the other portion of the cavity being formed by the inside wall of said escapement cylinder;

and when the shuttle is in said first position the cavity receiving said lip and the second conical surface being closely adjacent to said skirt; and the lip by filling said cavity and the close proximity of the skirt and second conical surface having the function of purging any air buttles trapped in said volumetric measuring chamber at the time said shuttle is moving from said second position down to said first position.

3. The construction of claim 1 wherein:

said first means is further formed with a cylindrical extension containing said drip passageway and with a pair of outwardly extending ears at the end of the drip passageway; and said check valve means being connected to the cylindrical extension with said ears extending into said exit passage and forming a part thereof, said ears having the function of minimizing bubble formation in the exit passage.

4. The construction of claim 1 wherein said drive means comprises:

a cylindrically shaped permanent magnet mounted in said shuttle with the axis of the magnet extending in the direction of motion of the shuttle;

a pair of U-shaped cores each having pole-forming drive winding thereon, the pair being respectively disposed on opposite sides of said escapement cylinder with the respective north poles when formed facing one another and the respective south poles when formed facing one another and the poles lying in a vertical plane containing the axis of the escapement cylinder; and in the first position of said shuttle, the lower end of the cylindrically shaped magnet being vertically positioned substantially at the midpoint between the north and south poles of the core magnets.

5. The construction of claim 4 wherein said drive means includes a compression spring inside of said escapement cylinder, the top end of the spring bearing on said spike and the lower end of the spring bearing on said shuttle, the spring functioning to assist in driving the shuttle from the second down to the first position, and maintaining a sealing pressure under all altitudes of the sealing chamber.

* * * * *